United States Patent
Steinø et al.

(10) Patent No.: US 11,717,505 B2
(45) Date of Patent: Aug. 8, 2023

(54) DIANHYDROGALACTITOL FOR THE TREATMENT OF DIFFUSE INTRINSIC PONTINE GLIOMAS

(71) Applicant: Del Mar Pharmaceuticals (BC) Limited, Vancouver (CA)

(72) Inventors: Anne Steinø, Vancouver (CA); Jeffrey A. Bacha, Vancouver (CA); Dennis M. Brown, Menlo Park, CA (US)

(73) Assignee: Del Mar Pharmaceuticals (BC) Limited, Vancouver (CA)

( * ) Notice: Subject to any disclaimer, the term of this patent is extended or adjusted under 35 U.S.C. 154(b) by 310 days.

(21) Appl. No.: 16/768,827

(22) PCT Filed: Nov. 2, 2018

(86) PCT No.: PCT/IB2018/001357
§ 371 (c)(1),
(2) Date: Jun. 1, 2020

(87) PCT Pub. No.: WO2019/106424
PCT Pub. Date: Jun. 6, 2019

(65) Prior Publication Data
US 2022/0226277 A1 Jul. 21, 2022

Related U.S. Application Data

(60) Provisional application No. 62/593,386, filed on Dec. 1, 2017, provisional application No. 62/652,702, filed on Apr. 4, 2018.

(51) Int. Cl.
| | |
|---|---|
| A61K 31/336 | (2006.01) |
| A61P 35/00 | (2006.01) |
| A61K 31/047 | (2006.01) |
| A61K 31/519 | (2006.01) |

(52) U.S. Cl.
CPC .......... *A61K 31/336* (2013.01); *A61K 31/047* (2013.01); *A61K 31/519* (2013.01); *A61P 35/00* (2018.01)

(58) Field of Classification Search
None
See application file for complete search history.

(56) References Cited

FOREIGN PATENT DOCUMENTS

| WO | 2013/110058 A2 | 7/2013 | |
| WO | WO-2017042634 A2 * | 3/2017 | ........... A61K 31/336 |
| WO | 2017/075052 A1 | 5/2017 | |

OTHER PUBLICATIONS

Erdélyi-Tóth et al, Cancer Chemotherapy and Pharmacology, vol. 16, pp. 257-263 (Year: 1986).*
Chiuten et al, Cancer, vol. 47, pp. 442-451, Feb. 1, 1981.*
Weitman et al, Investigational New Drugs. vol. 14, pp. 1-10 (Year: 1996).*
Caretti et al, Molecular Cancer Therapeutics, vol. 12, No. 2, pp. 141-150, Feb. 2013.*
Mueller, S., et al., "Targeting Wee1 for the Treatment of Pediatric High-Grade Gliomas," Neuro-Oncology 16(3):352-360, Dec. 2013.
Zhai, B., et al., "Dianhydrogalactitol (VAL-083) Overcomes Chemoresistance in Pediatric Malignant Brain Tumors and Displays Synergy with Topoisomerase Inhibitors," Neuro-Oncology 19(Supp6):vi195-vi196, Nov. 2017, abstract.
Zhai, B., et al., "Dianhydrogalactitol (VAL-083) Overcomes MGMT- and p53-Mediated Chemo-Resistance and Displays Synergy With Topoisomerase Inhibitors," Neuro-Oncology 19(Supp4):iv22-iv23, Jun. 2017, abstract.
International Search Report dated Apr. 12, 2019, issued in International Application No. PCT/IB2018/001357, filed Nov. 2, 2018, 8 pages.
International Written Opinion dated Apr. 12, 2019, issued in International Application No. PCT/IB2018/001357, filed Nov. 2, 2018, 8 pages.
International Preliminary Report on Patentability dated Jun. 2, 2020, issued in International Application No. PCT/IB2018/001357, filed Nov. 2, 2018, 8 pages.

* cited by examiner

*Primary Examiner* — Zinna Northington Davis
(74) *Attorney, Agent, or Firm* — Christensen O'Connor Johnson Kindness PLLC

(57) ABSTRACT

Methods for treating diffuse intrinsic pontine glioma (DIPG) comprising administration of a therapeutically effective amount of an alkylating hexitol (such as dianhydrogalacitol, diacetyldianhydrogalacitol, and dibromodulcitol) are disclosed. Such methods may further comprise administration of other anti-cancer agents. In preferred embodiments, the secondary anti-cancer agent is an inhibitor of Wee1 tyrosine kinase (such as adavosertib). Methods of treating malignancies in general comprising administration of a combination of an alkylating hexitol and an inhibitor of Wee1 tyrosine kinase are also disclosed.

11 Claims, 9 Drawing Sheets

DIANHYDROGALACTITOL FOR THE TREATMENT OF DIFFUSE INTRINSIC PONTINE GLIOMAS

CROSS-REFERENCE(S) TO RELATED APPLICATION(S)

This application is a National Stage of International Application No. PCT/IB2018/001357, filed Nov. 2, 2018, which claims the benefit of U.S. Provisional Application No. 62/593,386, filed Dec. 1, 2017 and U.S. Provisional Application No. 62/652,702, filed Apr. 4, 2018, the disclosures of which are expressly incorporated herein by reference in their entirety.

FIELD OF THE INVENTION

This invention is directed to the use of alkylating hexitols such as dianhydrogalactitol to treat diffuse intrinsic pontine glioma (DIPG), particularly in pediatric patients, either as a single agent or in combination with a Wee 1 inhibitor.

BACKGROUND OF THE INVENTION

Despite several decades of clinical trials, diffuse intrinsic pontine gliomas (DIPG) continue to have a poor outcome and survival remains dismal. DIPG is inoperable, and standard treatment is radiation alone, as the addition of chemotherapy has not improved survival. Major obstacles to the successful treatment of DIPG include an intact blood-brain barrier impeding drug penetration and inherent tumor-cell resistance mechanisms to chemotherapeutics.

This form of glioma is particularly prevalent in children. The majority of DIPG tumors contain mutations in the gene encoding histone H3, predominantly in variant H3.3 or H3.1. Patients with lysine to methionine mutations at amino acid 27 (K27M) in H3.1 or H3.3 have particularly poor prognoses (Mackay, A. et al., Integrated Molecular Meta-Analysis of 1,000 Pediatric High-Grade and Diffuse Intrinsic Pontine Glioma. Cancer Cell, Volume 32, ISSUE 4, P520-537.e5, Oct. 9, 2017). In addition, about 50% of DIPG tumors carry mutations in the gene for TP53. Currently, there is no cure for pediatric high grade gliomas such as DIPG, and 90% of children with this malignancy die within 18 months of diagnosis, 99% within 5 years of diagnosis.

Therefore, there is a need for an improved method to treat DIPG. Such a method should involve delivery of the active agent or agents to the affected regions of the brain and central nervous system and should be compatible with other treatment modalities, especially radiation. There is also a particular need for therapeutic modalities that can cross the blood-brain barrier (BBB), that can suppress the growth and division of cancer stem cells (CSC), and that can overcome resistance-mechanisms related to O6-methylguanine-DNA methyltransferase (MGMT).

SUMMARY OF THE INVENTION

In one aspect, provided herein is a method for treating diffuse intrinsic pontine glioma (DIPG), comprising the step of administering a therapeutically effective quantity of an alkylating hexitol to a patient with DIPG to treat the DIPG.

In certain embodiments, the alkylating hexitol is selected from the group consisting of dianhydrogalactitol, a derivative or analog of dianhydrogalactitol (DAG or VAL-083), diacetyldianhydrogalactitol (DADAG), a derivative or analog of diacetyldianhydrogalactitol, dibromodulcitol, and a derivative or analog of dibromodulcitol. In some embodiments, the alkylating hexitol is dianhydrogalactitol.

In some embodiments, the method further comprises administering a therapeutically effective quantity of an agent that requires malignant cells to be in the S/G2 phase of the cell cycle for its maximum therapeutic effect.

In certain embodiments, the method further comprises administering a therapeutically effective quantity of an inhibitor of Wee1 tyrosine kinase. Preferably, the inhibitor Wee1 tyrosine kinase is AZD1775 (formerly MK1775).

In another aspect, disclosed herein is a method of suppressing proliferation of diffuse intrinsic pontine glioma cell, comprising delivering or administering to the cell an alkylating hexitol, for example, dianhydrogalactitol, diacetyldianhydrogalactitol, or dibromodulcitol. In some embodiments, the alkylating hexitol is dianhydrogalactitol. In some embodiments, the cell is in vivo, for example, in a human subject. The administering can be done in vivo, for example, in a human subject with DIPG by administering a therapeutically effective quantity of an alkylating hexitol to the human subject.

The methods disclosed herein are particularly used for treatment of pediatric patients with DIPG. In some embodiments, the pediatric DIPG is p53 mutated DIPG, histone H3.3 K27M mutated DIPG, or histone H3.1 K27M mutated DIPG.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
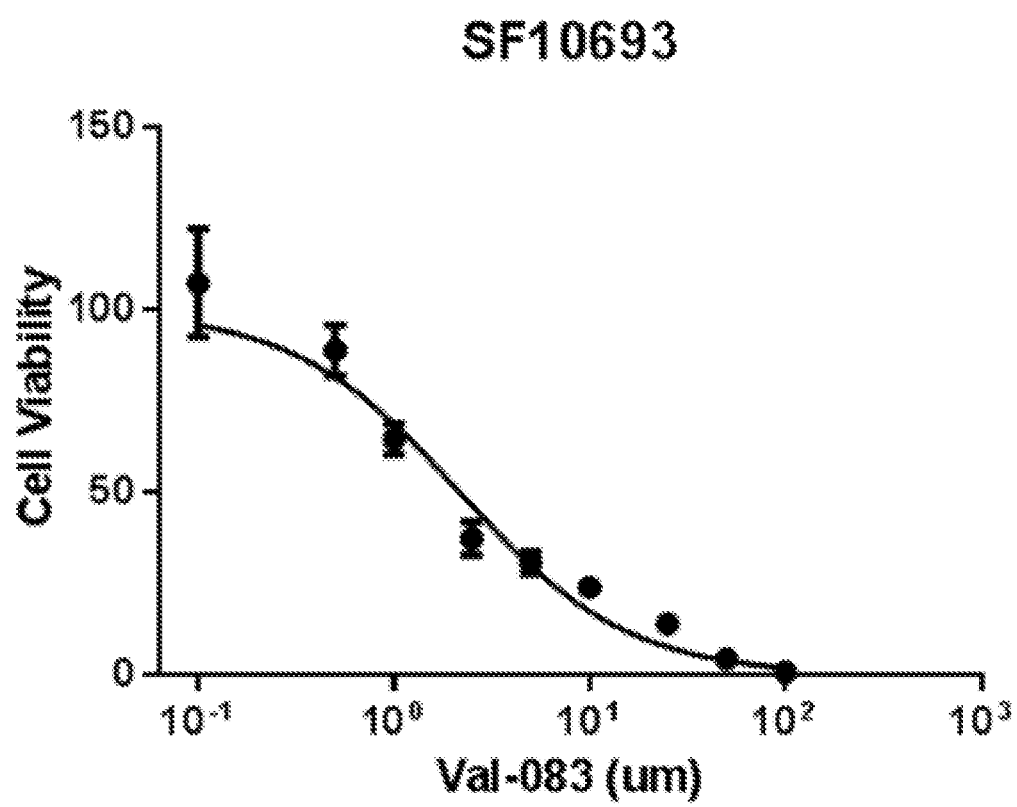
FIG. 1 shows VAL-083 activity against DIPG cell line SF10693 with histone 3.1 K27M mutation. The figure shows that VAL-083 was highly cytotoxic to the SF10693 cells with an IC50 of approximately 1 µM.

For the aspects described below relating to administration an alkylating hexitol derivative, typically, the alkylating hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol, unless otherwise specified. Preferably, the alkylating hexitol derivative is dianhydrogalactitol, unless otherwise specified. In some cases, derivatives of dianhydrogalactitol such as compound analogs or prodrugs are preferred, as stated below.

Alkylating hexitol derivatives that can be used in compositions and methods according to the present invention include galactitols, substituted galactitols, dulcitols, and substituted dulcitols. Typically, the alkylating hexitol derivative is selected from the group consisting of dianhydrogalactitol, derivatives of dianhydrogalactitol, analogs of dianhydrogalactitol, diacetyldianhydrogalactitol, derivatives of diacetyldianhydrogalactitol, analogs of diacetyldianhydrogalactitol, dibromodulcitol, derivatives of dibromodulcitol, and analogs of dibromodulcitol. More typically, the alkylating hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. In some embodiments, the alkylating hexitol derivative is dianhydrogalactitol. As used herein, the terms "substituted hexitol derivative," "alkylating hexitol derivative," and "alkylating hexitol" are used interchangeably herein and encompass these alternatives unless specifically limited to a compound, a compound with defined substituents, or a class of compounds within the broad definitions provided above.

In some embodiments, the alkylating hexitol is dianhydroglactitol, including its stereoisomers. The terms "dianhydrogalactitol," "DAG," and "VAL-083" are used herein interchangeably. The structure of dianhydrogalactitol (DAG or VAL-083) is shown in Formula (I), below.

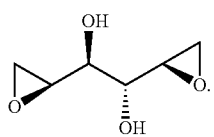

(I)

The galactitols, substituted galacitols, dulcitols, and substituted dulcitols included in the methods and combinations disclosed herein are either alkylating agents or prodrugs of alkylating agents, as discussed further below. Also within the scope of the invention are derivatives of dianhydrogalactitol that, for example, have one or both hydrogens of the two hydroxyl groups of dianhydrogalactitol replaced with lower alkyl, have one or more of the hydrogens attached to the two epoxide rings replaced with lower alkyl, or have the methyl groups present in dianhydrogalactitol and that are attached to the same carbons that bear the hydroxyl groups replaced with C2-C6 lower alkyl or substituted with, for example, halo groups by replacing a hydrogen of the methyl group with, for example a halo group. As used herein, the term "halo group," without further limitation, refers to one of fluoro, chloro, bromo, or iodo. As used herein, the term "lower alkyl," without further limitation, refers to C1-C6 groups and includes methyl. The term "lower alkyl" can be further limited, such as "C2-C6 lower alkyl," which excludes methyl. The term "lower alkyl", unless further limited, refers to both straight-chain and branched alkyl groups. These groups can, optionally, be further substituted, for example, with halo groups.

In some embodiments, the alkylating hexitol derivative is diacetyldianhydrogalactitol. The structure of diacetyldianhydrogalactitol is shown in Formula (II), below.

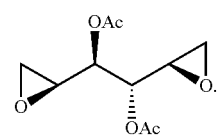

(I)

Also within the scope of the invention are derivatives of diacetyldianhydrogalactitol that, for example, have one or both of the methyl groups that are part of the acetyl moieties replaced with C2-C6 lower alkyl, have one or both of the hydrogens attached to the epoxide ring replaced with lower alkyl, or have the methyl groups attached to the same carbons that bear the acetyl groups replaced with lower alkyl or substituted with, for example, halo groups by replacing a hydrogen with, for example, a halo group.

In other embodiments, the alkylating hexitol derivative is dibromodulcitol of Formula (III):

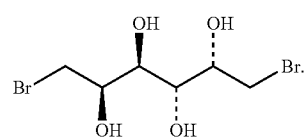

(III)

Dibromodulcitol can be produced by the reaction of dulcitol with hydrobromic acid at elevated temperatures, followed by crystallization of the dibromodulcitol. Some of the properties of dibromodulcitol are described in N. E. Mischler et al., "Dibromoducitol," *Cancer Treat. Rev.* 6: 191-204 (1979). In particular, dibromodulcitol, as an α,ω-dibrominated hexitol, dibromodulcitol shares many of the biochemical and biological properties of similar drugs such as dibromomannitol and mannitol myleran. Activation of dibromodulcitol to the diepoxide dianhydrogalactitol occurs in vivo, and dianhydrogalactitol may represent a major active form of the drug; this means that dibromogalactitol has many of the properties of a prodrug. Absorption of dibromodulcitol by the oral route is rapid and fairly complete.

Also within the scope of the invention are derivatives of dibromodulcitol that, for example, have one or more hydrogens of the hydroxyl groups replaced with lower alkyl, or have one or both of the bromo groups replaced with another halo group such as chloro, fluoro, or iodo.

The compounds described herein may contain one or more chiral centers and therefore, may exist as stereoisomers, such as enantiomers or diastereomers. The invention includes each of the isolated stereoisomeric forms (such as the enantiomerically pure isomers and other alternatives for stereoisomers) as well as mixtures of stereoisomers in varying degrees of chiral purity or percentage, including racemic mixtures and mixtures of diastereomers unless a specific stereoisomer is specified. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. When the chemical name does not specify the isomeric form of the compound, it denotes any one of the possible isomeric forms or mixtures of those isomeric forms of the compound.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

Additional derivatives of dianhydrogalactitol are known in the art. These derivatives include dimethyldianhydrogalactitol and disuccinyldianhydrogalactitol and are disclosed in Y. Zhou et al., "Research Progress in New Anti-Cancer Drugs with Hexitols," Chin. J. Cancer 12: 257-260 (1993).

In some alternatives, the derivative or analog of dianhydrogalactitol can be a prodrug. As used herein, the term "prodrug" refers to compounds that are transformed in vivo to yield a disclosed compound or a pharmaceutically acceptable form of the compound. In some embodiments, a prodrug is a compound that may be converted under physiological conditions or by solvolysis to a biologically active compound as described herein. Thus, the term "prodrug" refers to a precursor of a biologically active compound that is pharmaceutically acceptable. A prodrug can be inactive when administered to a subject, but is then converted in vivo to an active compound, for example, by hydrolysis (e.g., hydrolysis in blood or a tissue). In certain cases, a prodrug has improved physical and/or delivery properties over a parent compound from which the prodrug has been derived. The term "prodrug" is also meant to include any covalently bonded carriers which release the active compound in vivo when the prodrug is administered to a subject. Prodrugs of a therapeutically active compound, as described herein, can be prepared by modifying one or more functional groups present in the therapeutically active compound in such a way that the modifications are cleaved, either in routine manipulation or in vivo, to yield the parent therapeutically active compound.

Other Agents

In certain embodiments, the compositions and methods for treatments of DIPG disclosed herein include a combination of an alkylating hexitol derivative and an additional agent.

In some embodiments, the additional agent is a topoisomerase inhibitor. Topoisomerase inhibitors useful for inclusion in the compositions and methods disclosed herein include inhibitors of Type 1 topoisomerase and inhibitors of Type 2 topoisomerase. As alkylating hexitol derivatives, such as VAL-083, induce cell cycle arrest in S-followed by G2/M-phase, agents that require cancer cells to be in S/G2-phase for maximum effect, including topoisomerase inhibitors, can have synergistic effect with VAL-083.

Inhibitors of Type 1 topoisomerase include, but are not limited to, irinotecan, topotecan, camptothecin, homocamptothecin, DB 67 (7-t-butyldimethylsilyl-10-hydroxy-camptothecin), lamellarin D, indotecan, indimitecan, karenitecan, exatecan, lurtotecan, gimatecan, and belotecan, and others known in the art.

Inhibitors of Type 2 topoisomerase include two main classes: (i) topoisomerase poisons, which target the topoisomerase-DNA complex, and (ii) topoisomerase inhibitors, which disrupt catalytic turnover. Topoisomerase poisons that target eukaryotic topoisomerases include, but are not limited to, actinomycin D, daunomycin, amsacrine, etoposide, etoposide phosphate, teniposide, and doxorubicin. Topoisomerase inhibitors, which target the N-terminal ATPase domain of Type 2 topoisomerase and inhibit the turnover of the enzyme, include, but are not limited to, ICRF-193 (4-[2-(3,5-dioxo-1-piperazinyl)-1-methylpropyl]piperazine-2,6-dione) and genistein. Other inhibitors of Type 2 topoisomerase include, but are not limited to, amonafide and derivatives and analogs thereof, mitoxantrone, ellipticines, and aurintricarboxylic acid. Still other inhibitors of both Type 1 and Type 2 topoisomerase known in the art can be included in the compositions and their methods of use in DIPG treatment disclosed herein. In some embodiments, the topoisomerase inhibitor is irinotecan.

In some embodiments, the additional agent is a VEGF inhibitor. The VEGF inhibitor can, in one alternative, be a PPAR activator or agonist that indirectly inhibits the activity of VEGF. Some VEGF inhibitors that can be used in the methods and compositions disclosed herein include: (1) bevacizumab (Avastin) (monoclonal antibody); (2) ranibizumab (Lucentis) (monoclonal antibody Fab fragment); (3) lapatinib (tyrosine kinase inhibitor); (4) sunitinib (tyrosine kinase inhibitor) (5) sorafenib (tyrosine kinase inhibitor) (6) axitinib (tyrosine kinase inhibitor); (7) pazopanib (tyrosine kinase inhibitor); (8) tetrahydrocannabinol; (9) cannabidiol; (10) thiazolidinediones (including the following agents: rosiglitazone, pioglitazone, lobeglitazone, troglitazone, netoglitazone, rivoglitazone, and ciglitazone); and (11) withaferin A. Other VEGF inhibitors are also known in the art.

In some embodiments, the additional agent can be selected from the group consisting of: (i) an inhibitor of hexokinase II; (ii) a PFKFB3 inhibitor; (iii) an inhibitor of GAPDH; (iv) an inhibitor of PK-M2; (v) an inhibitor of glucose-6-phosphate isomerase; (vi) an inhibitor of LDH; (vii) an inhibitor of aldolase; (viii) an inhibitor of phosphoglycerate mutase; (ix) an inhibitor of enolase; (x) a MCT inhibitor; (xi) an agent that inhibits conversion of glutamate to α-ketoglutarate; (xii) an inhibitor of the cysteine-glutamate antiporter; (xiii) an inhibitor of NamPRT; (xiv) an agent to either restore p53 function or suppress activity of mutated p53; and (xv) an inhibitor of the pentose phosphate pathway (PPP).

Inhibitors of Wee1 Tyrosine Kinase

In certain embodiments, the compositions and methods for treatment of DIPG disclosed herein include a combination of an alkylating hexitol derivative and an inhibitor of Wee1 tyrosine kinase. In some embodiments, the inhibitor of Wee1 tyrosine kinase is AZD1775, which is also referred to as 2-allyl-1-(6-(2-hydroxypropan-2-yl)pyridin-2-yl)-6-((4-(4-methylpiperazin-1-yl)phenyl)-amino)-1H-pyrazolo [3,4-d]pyrimidin-3(2H)-one, AZD1775, MK-1775, or adavosertib. AZD1775 is a small molecule that selectively targets and inhibits Wee1, a tyrosine kinase that phosphorylates cyclin-dependent kinase 1 (CDK1, CDC2) to inactivate the CDC2/cyclin B complex. Inhibition of Wee1 activity prevents the phosphorylation of CDC2 and impairs the G2 DNA damage checkpoint. This may lead to apoptosis upon treatment with DNA damaging chemotherapeutic agents. Unlike normal cells, most p53 deficient or mutated human cancers lack the G1 checkpoint as p53 is the key regulator of the G1 checkpoint and these cells rely on the G2 checkpoint for DNA repair to damaged cells. Annulment of the G2 checkpoint may therefore make p53 deficient tumor cells more vulnerable to antineoplastic agents and enhance their cytotoxic effect. Approximately 50% of DIPG tumors harbor p53 mutations and thus rely on the G2 checkpoint for DNA repair.

Methods of Treatment

As used herein, the terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. The results of treatment can be determined by methods known in the art, such as determination of reduction of pain as measured by reduction of requirement for administration of opiates or other pain medication, determination of reduction of tumor burden, determination of restoration of function as determined by an improvement in the Karnofsky Performance Score, or other methods known in the art. The use of terms such as "treat" or "treatment" is not to be understood as implying a cure for any disease or condition.

As used herein, the term "synergistic," as used herein, refers to a therapeutic combination which is more effective than the additive effects of the two or more single agents. A determination of a synergistic interaction between: (i) dianhydrogalactitol, diacetyldianhydrogalactitol, or a derivative or analog thereof; and (ii) one or more additional chemotherapeutic agents may be assessed using assays as known in the art and, for example, can be analyzed using the Chou and Talalay combination method and Dose-Effect Analysis with CalcuSyn software in order to obtain a Combination Index (Chou and Talalay, 1984, *Adv. Enzyme Regul.* 22:27-55). Combination Index values less than 0.8 indicates synergy, values greater than 1.2 indicate antagonism, and values between 0.8 and 1.2 indicate additive effects. The combination therapy may provide "synergy" and prove "synergistic," i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes or using other routes of administration. In general, during alternation therapy, an effective dosage of each active ingredient is administered sequentially, i.e., serially, whereas in combination therapy, effective dosages of two or more active ingredients are administered together. Combination effects can also be evaluated using both the BLISS independence model and the highest single agent (HSA) model (Lehar et al. 2007, Molecular Systems Biology 3:80). BLISS scores quantify degree of potentiation from single agents and a BLISS score >0 suggests greater than simple additivity. In some alternatives, combination effects can be evaluated using both the BLISS independence model and the highest single agent (HSA) model (Lehar et al. 2007, Molecular Systems Biology 3:80). BLISS scores quantify degree of potentiation from single agents and a BLISS score >0 suggests greater than simple additivity. An HSA score >0 suggests a combination effect greater than the maximum of the single agent responses at corresponding concentrations. An HSA score >0 suggests a combination effect greater than the maximum of the single agent responses at corresponding concentrations.

In one aspect, provided herein is a method for treating diffuse intrinsic pontine glioma (DIPG), comprising the step of administering a therapeutically effective quantity of an alkylating hexitol to a patient with DIPG to treat the DIPG.

In certain embodiments, the alkylating hexitol is dianhydrogalactitol.

In some embodiments, the method further comprises administering a therapeutically effective quantity of an agent that requires malignant cells to be in the S/G2 phase of the cell cycle for its maximum therapeutic effect.

In certain embodiments, the method further comprises administering a therapeutically effective quantity of an inhibitor of Wee1 tyrosine kinase. Preferably, the Wee 1 inhibitor is AZD1775. As used herein, a "therapeutically effective dose" is a dose that is sufficient to achieve the intended purpose. In some embodiments, therapeutically effective dose of an agent administered in a combination with another agent or in combination with another method of treatment, e.g., surgery, can be lower than the dose of the agent administered alone.

The methods and compositions disclosed herein can be particularly useful for treatment of pediatric patients with DIPG. In some embodiments, the pediatric DIPG is p53 mutated DIPG, histone H3.3 K27M mutated DIPG, or histone H3.1 K27M mutated DIPG.

The methods and compositions disclosed herein can be employed as either first-line or second-line therapy or can be used as adjunct therapy or in combination with another method of DIPG treatment.

The amount of a given pharmacologically active agent, such as an alkylating hexitol derivative such as dianhydrogalactitol or an analog or derivative of dianhydrogalactitol as described above, or an inhibitor of Wee1 tyrosine kinase that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art.

As used herein, a "composition" can comprise one or more agents, such as DAG and an inhibitor of Wee1 tyrosine kinase. The composition can comprise each of the agents combined in a single container with a pharmaceutically acceptable carrier, or the composition can comprise each of the active agents in a separate container with a pharmaceutically acceptable carrier, which can be either the same or different, wherein the composition comprises a treatment regimen.

In some embodiments, the therapeutically effective quantities are the quantities of the alkylating hexitol derivative and the additional agent, such inhibitor of Wee1 tyrosine kinase, that produces synergism between the activities of the alkylating hexitol derivative and the additional agent.

Typically, in these compositions, the alkylating hexitol derivative is dianhydrogalactitol (DAG or VAL-083).

In some embodiments, disclosed herein is a method of suppressing proliferation of diffuse intrinsic pontine glioma cell, comprising administering to the cell an alkylating hexitol, for example, dianhydrogalactitol, diacetyldianhydrodulcitol, or dibromodulcitol. In some embodiments, the alkylating hexitol is dianhydrogalactitol. The administering or contacting can be done in vivo, for example, in a human subject by administering a therapeutically effective quantity of an alkylating hexitol to the human subject in need thereof.

When multiple therapeutic agents are administered according to the methods disclosed herein, each therapeutic agent can be administered separately, or two or more therapeutic agents can be administered in a single pharmaceutical composition. For example, when three therapeutic agents are to be administered, the following possibilities exist. (1) Each of the three therapeutic agents is administered individually; in this case, each agent can be administered in a separate pharmaceutical composition or as the agent alone without use of a pharmaceutical composition for the agent. (2) Two of the therapeutic agents are administered together in a single pharmaceutical composition, while the third therapeutic agent is administered separately, either as the agent alone or in a separate pharmaceutical composition. (3) All three therapeutic agents are administered together in a single pharmaceutical composition.

The amount of a given pharmacologically active agent, such as an alkylating hexitol derivative such as dianhydrogalactitol or an analog or derivative of dianhydrogalactitol as described above, that is included in a unit dose will vary depending upon factors such as the particular compound, disease condition and its severity, the identity (e.g., weight) of the subject in need of treatment, but can nevertheless be routinely determined by one skilled in the art.

Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures can involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. If a liquid carrier is used, the preparation will be in the form of syrup, emulsion, soft gelatin capsule, sterile injectable solution or suspension in an ampoule or vial or non-aqueous liquid suspension.

In some embodiments, the agent can be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In some embodiments, the agent is in an appropriate aqueous vehicle such as water or isotonic saline or dextrose solution.

In some embodiments, the alkylating hexitol is administered to a subject in need thereof in a pharmaceutical formulation comprising one or more excipients. Any suitable formulations can be used. For example, in some embodiments, the alkylating hexitol is in lyophilized form. Lyophilized dosage fills well known in the art. In some embodiments, preparation of lyophilized dosage forms of dianhydrogalactitol, dibromodulcitol, diacetyldianhydrogalactitol, and derivatives thereof, comprises the following steps:

(1) Dissolve the drug in water for injection precooled to below 10° C. Dilute to final volume with cold water for injection to yield a 40 mg/mL solution.

(2) Filter the bulk solution through a 0.2-μm filter into a receiving container under aseptic conditions. The formulation and filtration should be completed in 1 hour.

(3) Fill nominal 1.0 mL filtered solution into sterilized glass vials in a controlled target range under aseptic conditions.

(4) After the filling, all vials are placed with rubber stoppers inserted in the "lyophilization position" and loaded in the prechilled lyophilizer. For the lyophilizer, shelf temperature is set at +5° C. and held for 1 hour; shelf temperature is then adjusted to −5° C. and held for one hour, and the condenser, set to −60° C., turned on.

(5) The vials are then frozen to 30° C. or below and held for no less than 3 hours, typically 4 hours.

(6) Vacuum is then turned on, the shelf temperature is adjusted to −5° C., and primary drying is performed for 8 hours; the shelf temperature is again adjusted to −5° C. and drying is carried out for at least 5 hours.

(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.

(8) Break the vacuum with filtered inert gas (e.g., nitrogen). Stopper the vials in the lyophilizer.

(9) Vials are removed from the lyophilizer chamber and sealed with aluminum flip-off seals. All vials are visually inspected and labeled with approved labels.

In some embodiments, the lyophilized alkylating hexitol is reconstituted in sterile saline for injection. The required dose then can be diluted further into a pre-determined volume of sterile saline, e.g., 500 ml of saline, and infused intravenously over a specified period, for example, over 120 minutes, 60 minutes, or 30 minutes.

It will be appreciated that the actual dosages of the agents used in the methods and compositions disclosed herein will vary according to the particular agent being used, the particular composition formulated, and the mode of administration and the particular site.

The other agents, such as an inhibitor of Wee1 tyrosine kinase, can be administered at the same time or close together in time as an alkylating hexitol derivative. The dosages of the dianhydrogalactitol and the other agent can be selected to provide a synergistic or superadditive effect. The dose can be further optimized as disclosed above.

The compositions of the invention can be manufactured using techniques generally known for preparing pharmaceutical compositions, e.g., by conventional techniques such as mixing, dissolving, granulating, dragee-making, levitating, emulsifying, encapsulating, entrapping or lyophilizing Pharmaceutical compositions may be formulated in a conventional manner using one or more physiologically acceptable carriers, which may be selected from excipients and auxiliaries that facilitate processing of the active compounds into preparations, which can be used pharmaceutically.

The compounds can be formulated for parenteral administration by injection, e.g., by bolus injection or continuous infusion. Formulations for injection may be presented in unit-dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects can continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For the purposes of the present application, treatment can be monitored by observing one or more of the improving symptoms associated with the disease, disorder, or condition being treated, or by observing one or more of the improving clinical parameters associated with the disease, disorder, or condition being treated. As used herein, the terms "treatment," "treating," or equivalent terminology are not intended to imply a permanent cure for the disease, disorder, or condition being treated.

EXAMPLES

The following experiments were carried out: (1) evaluation of dose-response relationships for efficacy of dianhydrogalactitol in in vitro models of DIPG using different patient-derived models based on the genetic mutations presents in these tumors; and (2) evaluation of dose-response relationships for efficacy of dianhydrogalactitol in combination with other agents such as a Wee1 inhibitor AZD1775 in in vitro models of DIPG using different patient derived models based on the genetic mutations presents in these tumors. The cell lines used in the in vitro experiments were: p53 mutated DIPG (NEM157), histone H3.3 K27M mutated DIPG (NEM157 and SF8628), and histone H3.1 K27M mutated DIPG (SF10693).

In Vitro Proliferation/Viability Study

The Proliferation/Viability effects of VAL-083 alone, or combination treatment with Wee1 inhibitor AZD1775 (Selleckchem, in DMSO) on DIPG biopsy-derived tumor cells were quantified using CellTiter-Glo® Luminescent Cell Viability Assay Kit. One thousand cells were placed into each well as single cells in triplicate in a 96-well flat clear-bottomed plate (Corning Inc., Costar), and allowed to adhere for 24 hours in incubation at 37° C. and 5% $CO_2$. Cells were then treated with different concentration of VAL-083 alone or combination treatment. Phosphate buffered saline (PBS) was used to dissolve VAL-083 (dissolved in DMSO), and as control with the appropriate amount of DSMO. VAL-083 was provided from DelMar. Luminescence was read using a BioTek Synergy Plate Reader 72 hours after treatment. Data and statistical analysis were performed using GraphPad Prism.

Figure 2:
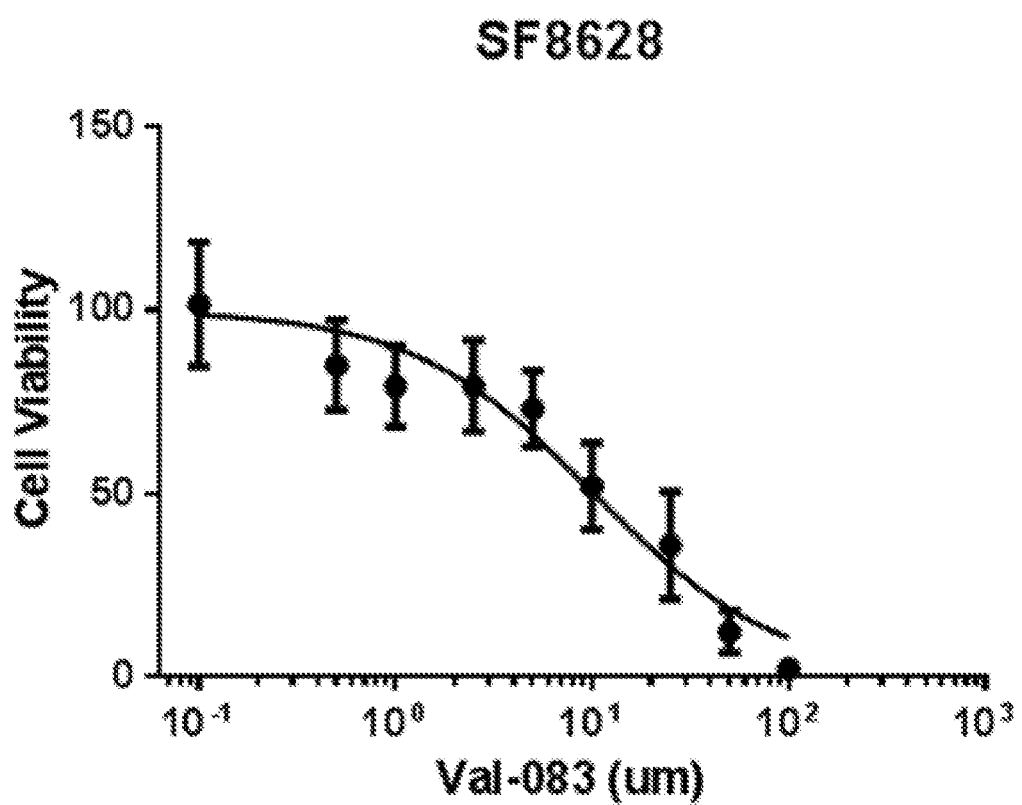
FIG. 2 shows VAL-083 activity against DIPG cell line SF8628 with histone 3.3 K27M mutation. The figure shows that VAL-083 was highly cytotoxic to the SF8628 cells with an IC50 of approximately 5 µM.
Figure 3:
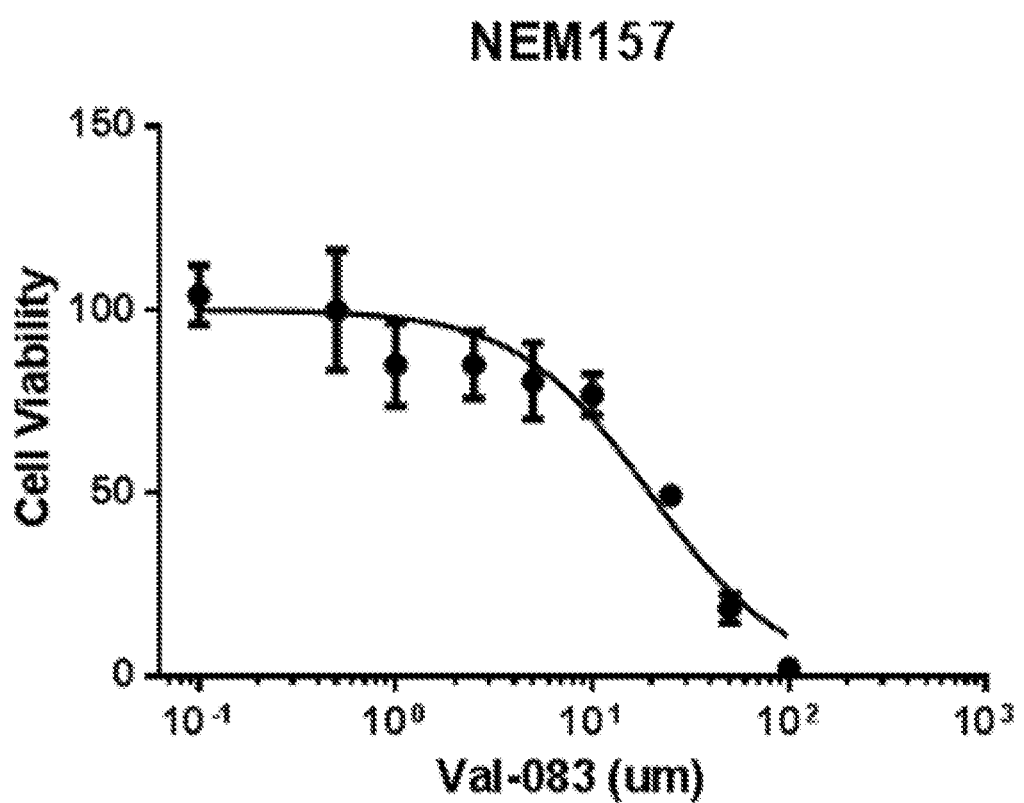
FIG. 3 shows VAL-083 activity against DIPG cell line NEM157 with histone 3.3 K27M mutation and p53 mutation. The figure shows that VAL-083 was highly cytotoxic to the NEM157 cells with an IC50 of approximately 10 µM.
Figure 4:
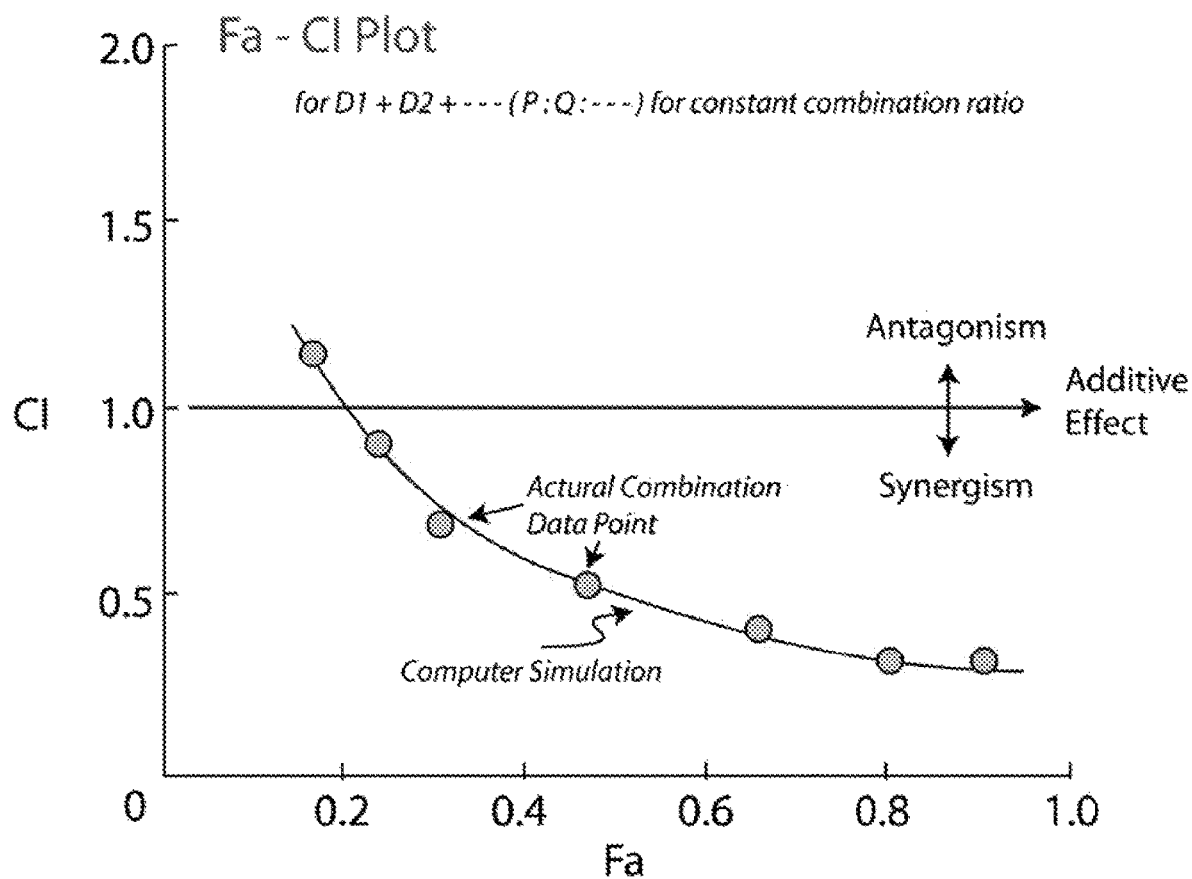
FIG. 4 shows a hypothetical combination index plot (FA CI plot) for a set of two combinations. The graph shows how to interpret an FA CI plot to assess synergy.
Figure 5:
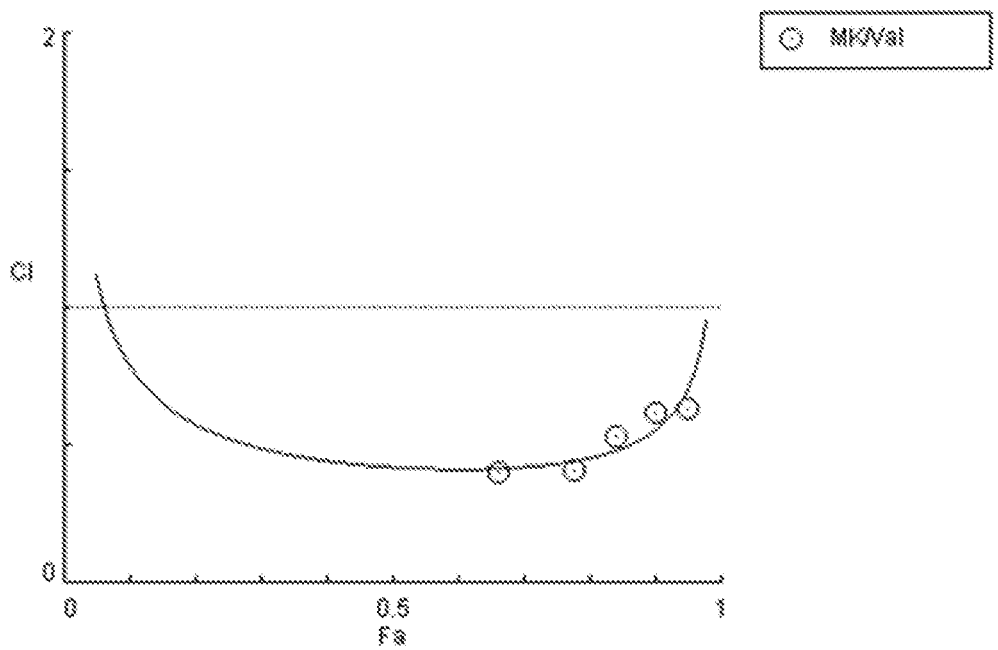
FIG. 5 shows an FA CI plot for the combination of VAL-083 and Wee1 inhibitor AZD1775 against DIPG cell line SF8629. The table below the figure shows the concentrations used of VAL-083 and AZD1775. The FA CI plot shows strong synergy between VAL-083 and AZD1775 in SF8629.
Figure 6:
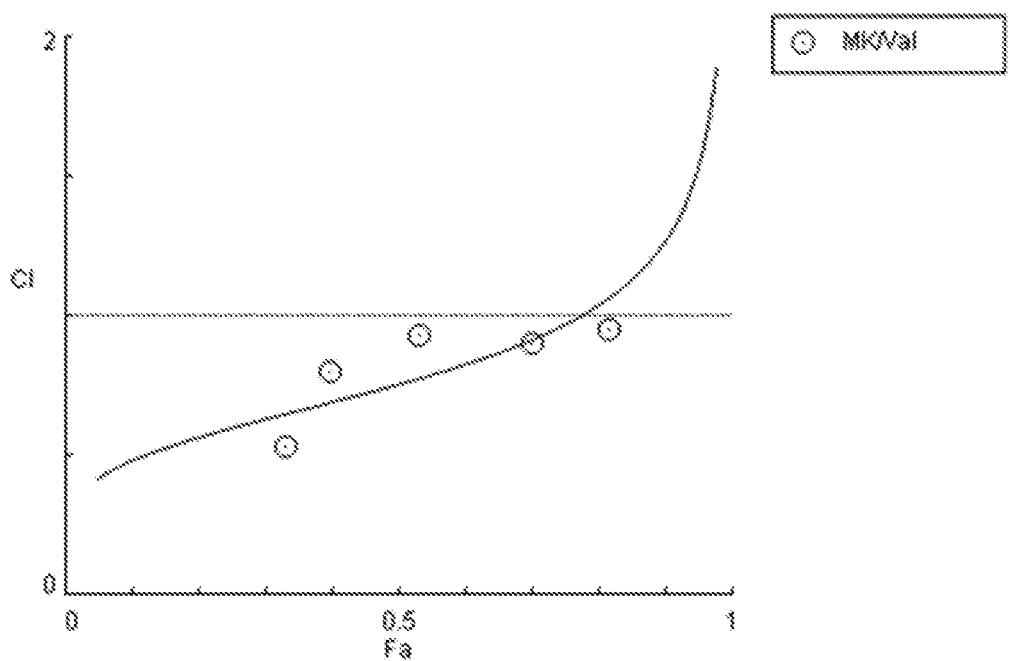
FIG. 6 shows an FA CI plot for the combination of VAL-083 and Wee1 inhibitor AZD1775 against DIPG cell line NEM157. The table below the figure shows the concentrations used of VAL-083 and AZD1775. The FA CI plot shows mild synergy between VAL-083 and AZD1775 in NEM157.

The results of the study are shown in FIGS. 1-3 and 5-6.

Summary of Results

The inventors investigated the effects of VAL-083 alone or in combination with AZD1775 in three DIPG cell-lines: SF10693 (H3.1), SF8628 (H3.3) and NEM157 (H3.3). VAL-083 showed activity at low uM-concentration in all three cell-lines. In addition, VAL-083 showed synergy or strong synergy with AZD1775 in all three DIPG cell-lines. Combined with its ability to cross the BBB, accumulate in brain tumor tissue and overcome MGMT-related chemoresistance, these results demonstrate that VAL-083 can be used as a treatment option for DIPG as single agent or in combination with AZD1775.

In Vivo Study of VAL-083 and AZD1775 Activity in Murine Pediatric DIPG Model

In vivo activity of VAL-083 as single agent and in combination with AZD1775 was assessed in an orthotopic engraftment model of pediatric DIPG (SF8628). For the anti-cancer dose-response relationship for dianhydrogalactitol alone and in combination with inhibitor of Wee1 tyrosine kinase AZD1775 in murine orthotropic pediatric DIPG tumor models, four treatment groups were used: control, VAL-083 alone, AZD1775 alone, and VAL-083 combination with AZD1775. For each treatment group, n=10 (8 mice for efficacy and OS measures and 2 mice per group for IHC and WB assessment) was chosen. The endpoints included clinical signs, body weight, tumor volume/bioluminescence, and survival.

Five six week-old female athymic nude mice were purchased from Envigo and housed under aseptic conditions. Luciferase-modified SF8628 tumor cells were implanted into the pontine tegmentum of the mice (total of 1.0× 105SF8628 cells in 1 μL volume). Tumor growth in vivo was monitored using bioluminescence imaging performed with the Xenogen IVIS Lumina System using Living Image software for data acquisition (Xenogen). Tumor-bearing mice were randomized to one of the following treatment groups: (i) vehicle control; (ii) VAL-083; (iii) AZD1775; (iv) VAL-083+AZD1775. Animals were treated with 60 mg/kg AZD1775 daily by oral administration (Mon-Fri), 3 mg/kg VAL-083 per day by IP every other day (Mon-Wed-Fri), and the treatment continued until animals reached the endpoint.

Figure 7A:
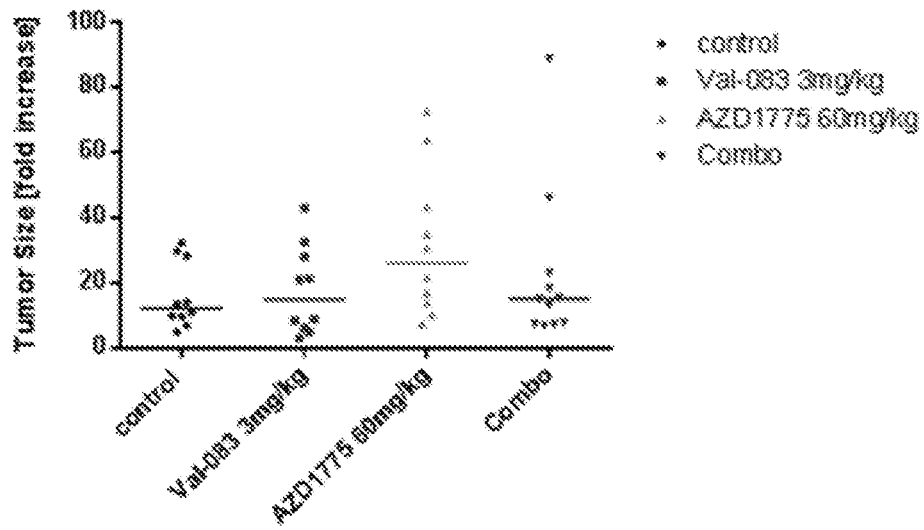
FIGS. 7A-D show tumor size increase in mice with engrafted DIPG tumors of SF8628 origin on day 21 (FIG. 14A), day 28 (FIG. 14B), day 35 (FIG. 14C) and day 43 (FIG. 14D) after tumor cell inoculation. Mice were treated with either control saline, VAL-083 alone, Wee1 inhibitor AZD1775 alone, or a combination of VAL-083 and AZD1775 and tumors were measured weekly by bioluminescence imaging. Tumor size was significantly reduced in animals treated with VAL-083 as single agent or VAL-083 in combination with AZD1775 on days 35 and 43 compared to control and to AZD1775 alone.
Figure 7B:
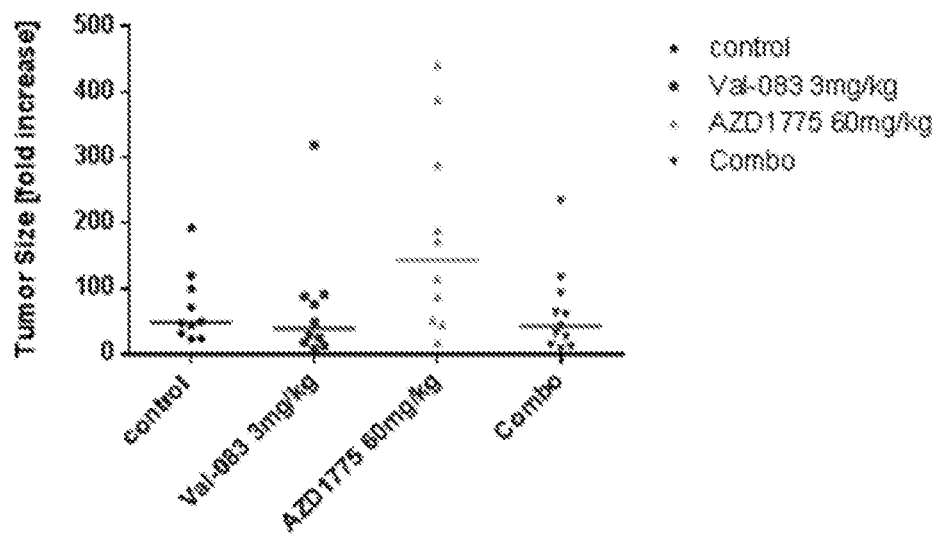
Figure 7C:
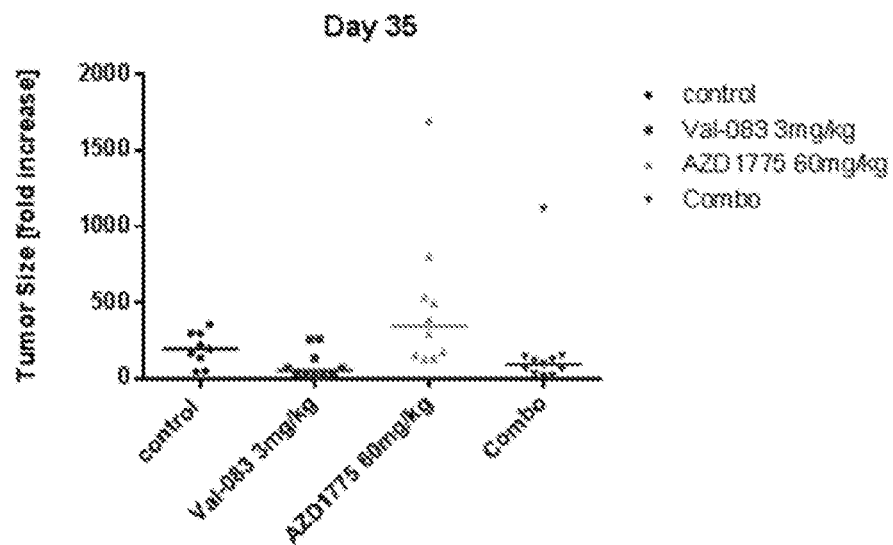
Figure 7D:
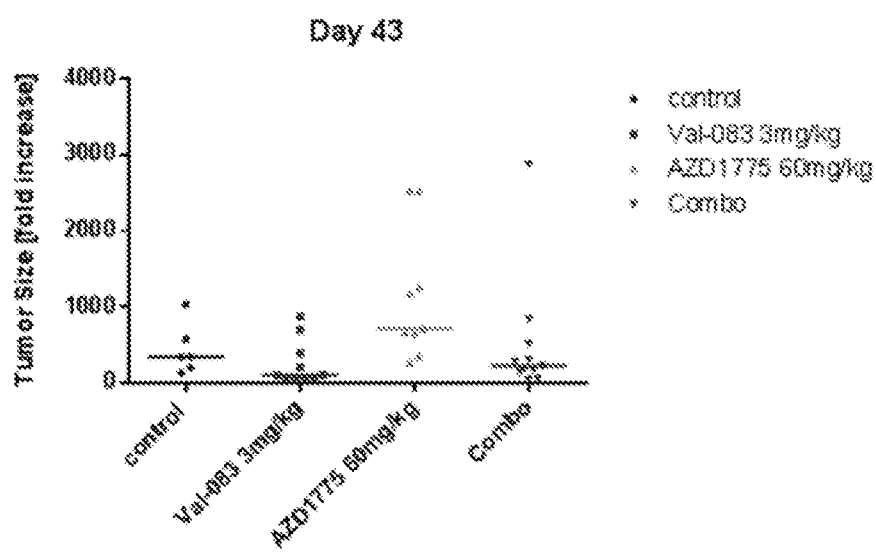
Figure 8:
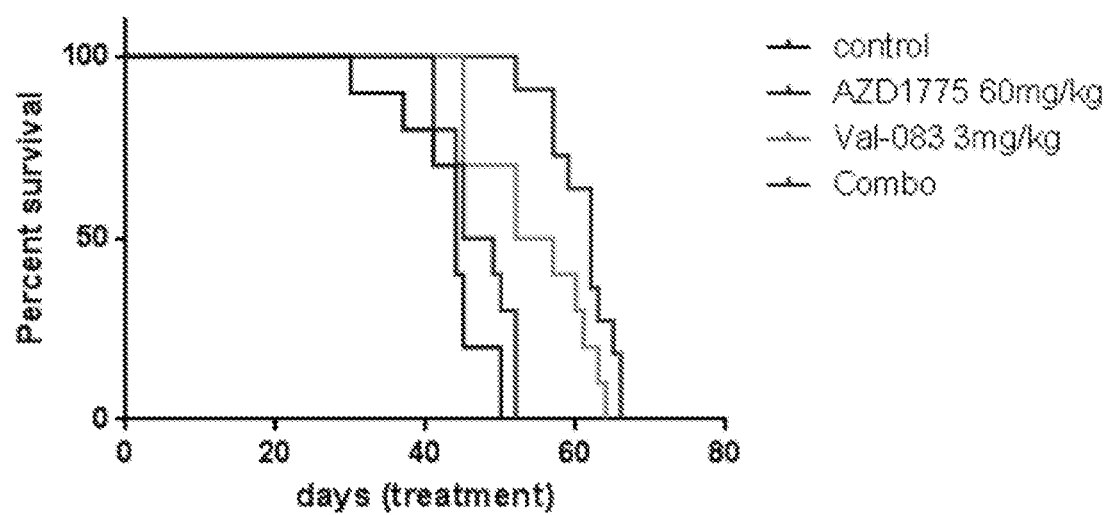
FIG. 8 is a Kaplan-Meier survival plot for four groups of mice bearing pediatric DIPG tumors of SF8628 origin: control group, mice treated with AZD1775 (60 mg/kg) as single agent, mice treated with VAL-083 (3 mg/kg) as single agent, and mice treated with the combination of AZD1775 and VAL-083. The study showed that combined treatment with VAL-083/AZD1775 combination conferred significantly greater survival benefit to mice with engrafted DIPG tumors compared to control as well as single agent treatment with AZD1775. The median survival for mice treated with VAL-083 alone was 54.5 days and for the VAL-083/AZD1775 combination it was 62 days, compared to 44 days for the control group and 47 days for mice treated with AZD1775 alone.

GraphPad software was used to generate Kaplan-Meier survival curves, and differences between survival curves were calculated using a log-rank test. The results of the study are shown in FIGS. 7A-7D and 8 and survival data is summarized in Table 1.

TABLE 1

Median survival of mice engrafted with DIPG tumors of SF8628 origin.

| Group | Control | AZD1775 60 mg/kg | VAL-083 3 mg/kg | VAL-083 and AZD1775 |
|---|---|---|---|---|
| Median survival | 44 | 47 | 54.5 | 62 |

| | p-value |
|---|---|
| VAL-083 vs. control | 0.0004 |
| AZD1775 vs. control | 0.0839 |
| VAL-083 vs. AZD1775 | 0.0101 |
| VAL-083/AZD1775 vs. control | <0.0001 |
| VAL-083/AZD1775 vs. VAL-083 | 0.0401 |
| VAL-083/AZD1775 vs. AZD1775 | <0.0001 |

Summary of Results

The study showed that combined treatment with VAL-083 and AZD1775 conferred significantly greater survival benefit to mice with engrafted DIPG tumors compared to control as well as single agent treatment with AZD1775. A significant survival benefit in this SF8628 PDX DIPG model was observed with VAL-083 (3 mg/kg) as single agent and as part of a combination with inhibitor of Wee1 tyrosine kinase AZD1775 (60 mg/kg). The median survival for mice treated with VAL-083 alone was 54.5 days and for the VAL-083/AZD1775 combination it was 62 days, compared to 44 days for control and 47 days for mice treated with AZD1775 alone.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including issued patents, published patent publications, and journal articles, are incorporated herein by this reference.

While illustrative embodiments have been illustrated and described, it will be appreciated that various changes can be made therein without departing from the spirit and scope of the invention The embodiments of the invention in which an exclusive property or privilege is claimed are defined as follows:

1. A method for treating a diffuse intrinsic pontine glioma (DIPG) in a patient, the method comprising administering a therapeutically effective quantity of an alkylating hexitol derivative to the patient with DIPG.

2. The method of claim 1, wherein the alkylating hexitol derivative is dianhydrogalactitol, diacetyldianhydrogalactitol, or dibromodulcitol.

3. The method of claim 1, wherein the alkylating hexitol derivative is dianhydrogalactitol.

4. The method of claim 1, wherein the patient with DIPG is a pediatric patient.

5. The method of claim 1, wherein the method further comprises administering a therapeutically effective quantity of an agent that requires malignant cells to be in the S/G2 phase of the cell cycle for its maximum therapeutic effect.

6. The method of claim 1, wherein the method further comprises administering a therapeutically effective quantity of an inhibitor of Wee1 tyrosine kinase.

7. The method of claim 6, wherein the inhibitor of Wee1 tyrosine kinase is AZD1775.

8. The method of claim 1, wherein the DIPG is p53-mutated DIPG, histone H3.3 K27M-mutated DIPG, histone H3.1 K27M-mutated DIPG, or DIPG with a p53 mutation and a H3.3 K27M mutation.

9. The method of claim 6, wherein the alkylating hexitol derivative and the inhibitor of Wee1 tyrosine kinase are administered in any sequential order.

10. The method of claim 6, wherein the alkylating hexitol derivative and the inhibitor of Wee1 tyrosine kinase are administered on different days.

11. The method of claim 6, wherein the alkylating hexitol derivative and the inhibitor of Wee1 tyrosine kinase are administered on the same days.

\* \* \* \* \*